United States Patent
Ehlis

(10) Patent No.: US 11,046,814 B2
(45) Date of Patent: Jun. 29, 2021

(54) ULTRAVIOLET RADIATION ABSORBING POLYMER COMPOSITION

(71) Applicant: BASF SE, Ludwigshafen am Rhein (DE)

(72) Inventor: Thomas Ehlis, Basel (CH)

(73) Assignee: BASF SE, Ludwigshafen am Rhein (DE)

( * ) Notice: Subject to any disclaimer, the term of this patent is extended or adjusted under 35 U.S.C. 154(b) by 55 days.

(21) Appl. No.: 16/338,526

(22) PCT Filed: Oct. 2, 2017

(86) PCT No.: PCT/EP2017/074931
§ 371 (c)(1),
(2) Date: Apr. 1, 2019

(87) PCT Pub. No.: WO2018/065341
PCT Pub. Date: Apr. 12, 2018

(65) Prior Publication Data
US 2020/0299459 A1  Sep. 24, 2020

(30) Foreign Application Priority Data

Oct. 5, 2016  (EP) .................................. 16192444

(51) Int. Cl.
| | |
|---|---|
| C08F 2/46 | (2006.01) |
| C08F 2/50 | (2006.01) |
| C08G 61/04 | (2006.01) |
| C08G 65/48 | (2006.01) |
| A61K 8/85 | (2006.01) |
| A61Q 17/04 | (2006.01) |
| C09B 69/10 | (2006.01) |

(52) U.S. Cl.
CPC ............... C08G 65/48 (2013.01); A61K 8/85 (2013.01); A61Q 17/04 (2013.01); C09B 69/109 (2013.01)

(58) Field of Classification Search
CPC ........ C09B 69/109; C08G 65/48; A61K 8/85; A61Q 17/04
USPC ................... 522/6, 189, 184, 71, 1; 520/1
See application file for complete search history.

(56) References Cited

U.S. PATENT DOCUMENTS

| | | |
|---|---|---|
| 6,620,904 B2 | 9/2003 | Lemke |
| 2002/0058781 A1 | 5/2002 | Lemke |
| 2004/0247536 A1 | 12/2004 | Chaudhari |
| 2006/0235116 A1 | 10/2006 | Lazzari et al. |
| 2010/0209463 A1 | 8/2010 | Pfluecker et al. |
| 2014/0004063 A1 | 1/2014 | Daly |

(Continued)

FOREIGN PATENT DOCUMENTS

| | | |
|---|---|---|
| DE | 1165574 B | 3/1964 |
| DE | 2024051 A1 | 12/1971 |

(Continued)

OTHER PUBLICATIONS

International Search Report for PCT/EP2017/074931 dated Oct. 27, 2017.

(Continued)

*Primary Examiner* — Jessica Whiteley
(74) *Attorney, Agent, or Firm* — Faegre Drinker Biddle & Reath LLP

(57) ABSTRACT

Disclosed is a method for preparing an ultraviolet radiation absorbing polymer composition comprising the polymer compound of formula (3)

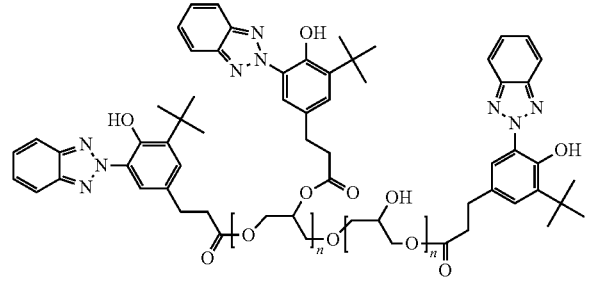

in an esterification/transesterification which method comprises the steps of reacting a polyglycerol intermediate of formula (2)

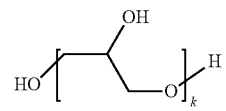

with a benzotriazole UV-chromophore comprising a complementary functional group of formula (1)

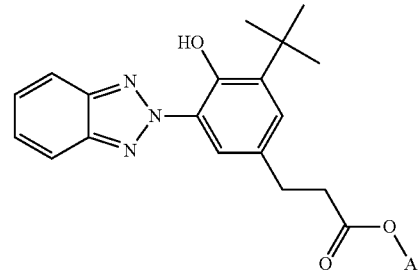

to form the polymer compound of formula (3).

20 Claims, No Drawings

(56) References Cited

U.S. PATENT DOCUMENTS

| | | | | |
|---|---|---|---|---|
| 2014/0004064 | A1* | 1/2014 | Daly | A61K 8/55 424/59 |
| 2015/0164771 | A1* | 6/2015 | Daly | A61Q 17/04 424/59 |
| 2015/0320671 | A1* | 11/2015 | Daly | A61K 8/86 424/59 |

FOREIGN PATENT DOCUMENTS

| | | | |
|---|---|---|---|
| DE | 10138496 | A1 | 2/2003 |
| DE | 10229995 | A1 | 1/2004 |
| DE | 102007035567 | A1 | 1/2009 |
| EP | 1371356 | A2 | 12/2003 |
| EP | 1371357 | A2 | 12/2003 |
| EP | 1371358 | A2 | 12/2003 |
| EP | 2679616 | * | 6/2013 |
| EP | 2679616 | A1 | 1/2014 |
| EP | 2886101 | A1 | 6/2015 |
| FR | 2252840 | A1 | 6/1975 |
| GB | 962919 | A | 7/1964 |
| GB | 1333475 | A | 10/1973 |
| GB | 1494915 | A | 12/1977 |
| RU | 2370502 | C2 | 10/2009 |
| WO | WO-2002036534 | A2 | 5/2002 |
| WO | WO-2002039974 | A1 | 5/2002 |
| WO | WO-0341675 | A2 | 5/2003 |
| WO | WO-2007092407 | A2 | 8/2007 |
| WO | WO-2009012871 | A2 | 1/2009 |
| WO | WO-2010136360 | A2 | 12/2010 |
| WO | WO-2011003774 | A2 | 1/2011 |
| WO | WO-2011098315 | A1 | 8/2011 |
| WO | WO-2015122770 | A1 | 8/2015 |
| WO | WO-2017218390 | A1 * | 12/2017 ............... A61K 8/86 |

OTHER PUBLICATIONS

Written Opinion of the International Searching Authority for PCT/EP2017/074931 dated Oct. 27, 2017.
U.S. Appl. No. 16/302,466, filed Nov. 16, 2018.
European Search Report for EP Patent Application No. 16192444.4, dated Feb. 23, 2017, 4 pages.

* cited by examiner

ULTRAVIOLET RADIATION ABSORBING POLYMER COMPOSITION

CROSS-REFERENCE TO RELATED APPLICATIONS

This application is a national stage application (under 35 U.S.C. § 371) of PCT/EP2017/074931, filed Oct. 2, 2017, which claims benefit of European Application No. 16192444.4, filed Oct. 5, 2016, both of which are incorporated herein by reference in their entirety.

The present invention relates to a method for preparing an ultraviolet radiation, absorbing polymer composition comprising the polymer compound of formula (3) in an esterification/transesterification which method comprises the steps of reacting a polyglycerol intermediate (2) with a benzotriazole UV-chromophore (1) comprising a complementary functional, group to form the polymer compound (3) according to the following reaction scheme:

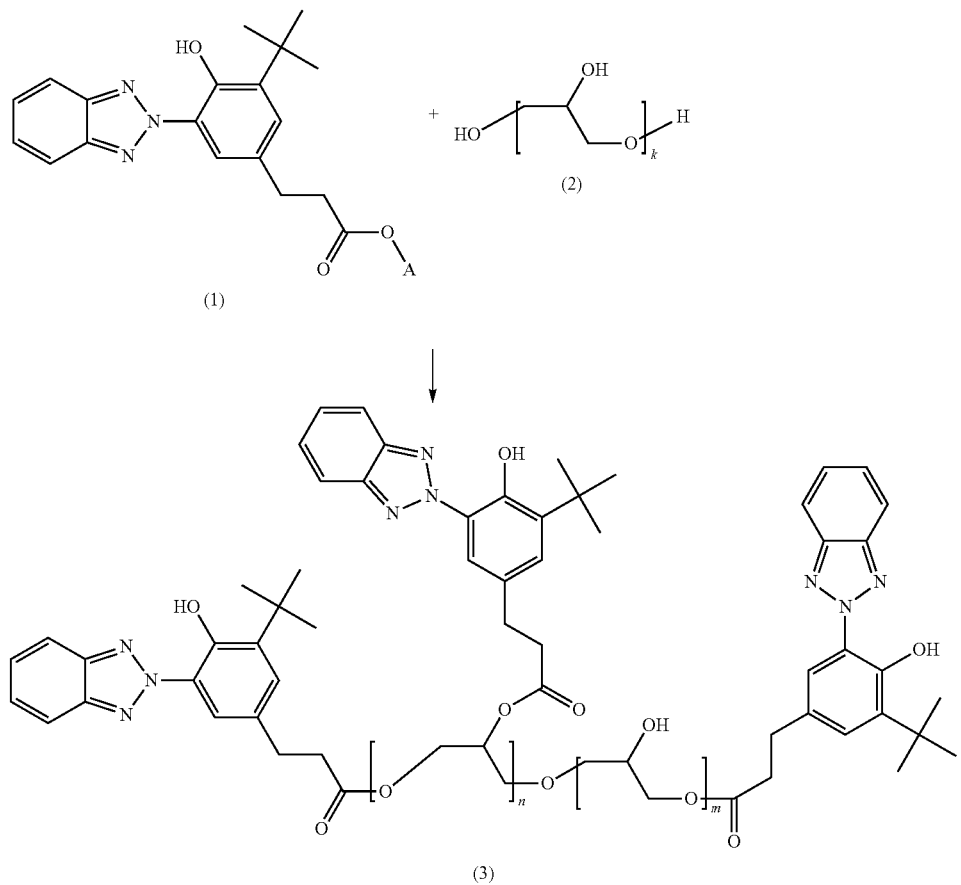

wherein
A is hydrogen; or $C_1$-$C_8$alkyl; and
k is a number from 1 to 20; and
n and m, independently from each other are a number from 0 to 20; wherein at least one of m and n is $\geq 1$.

The polymer compound of formula (3) represents a UV absorbing polyether that absorbs radiation in wavelengths between 290 and 400 nm. The UV absorbing polyether has a weight average molecular weight (M), which may be suitable for reducing or preventing the chromophore from absorbing through the skin. According to one preferred embodiment, a suitable molecular weight for the UV absorbing polyether is M>500. In a more preferred embodiment, M is in the range of about 500 to about 50,000. In another preferred embodiment, M is in the range of about 1,000 to about 20,000, such as from about 1,000 to about 10,000.

Polyglycerol (CAS Registry Number 25618-55-7; 1, 2, 3-Propanetriol, homopolymer) is known as a versatile building block for sustainable cosmetic raw materials (Wenk, H. H.; Meyer, J.; SOFW Journal, 2009, volume 135, issue 8, pages 25-30).

Polyglycerol is an ether linked homopolymer of glycerol, which is available in different degrees of polymerization, where higher polymers are associated with increasing hydrophilicity and molecular weight. Although the idealized structure of polyglycerol—a 1,3-linked, linear polymer—is rather simple, the reality is much more complex. Polyglycerols are mixtures of a number of structures, which are defined by oligomer distribution, degree of branching, and amount of cyclic structures. Even products with the same average molecular weight may differ significantly in their properties.

The oligomerization of glycerol is a consecutive reaction, and complete conversion of glycerol favours formation of high molecular-weight glycerol oligo—and polymers.

The general structural formula for polyglycerol can be sketched as

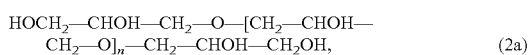

wherein
  n=0 results in diglycerol,
  n=1 in triglycerol, n=2 in tetraglycerol etc., including branched isomers formed by reaction of secondary hydroxyls.

Beside linear polyglycerol, cyclic oligomers can be formed by further condensation (Diglycerin and hoehere Oligomere des Glycerins als Synthesebausteine, Jakobson, G., Fette, Seifen Anstrichmittel, 1986, volume 88, pages 101-106).

With increase of molecular weight the hydroxyl number of polyglycerol decreases (diglycerol comprises 4, triglycerol 5, tetraglycerol 6 etc. hydrox groups). In some embodiments, the glycerol-based composition is fractionated to produce the desired distribution of glycerol polymers and a desired hydroxyl value.

Detailed synthesis procedures for the preparation of polyglycerol are described in WO2011098315, WO2015122770, WO2002036534, US20020058781, U.S. Pat. No. 6,620,904 and WO2007092407.

Preferred catalysts for the preparation of polyglycerin are $K_2CO_3$, $Li_2CO_3$, $Na_2CO_3$, KOH, NaOH, $CH_3ONa$, Ca$(OH)_2$, LiOH, $MgCO_3$, MgO, CaO, $CaCO_3$, ZnO, CsOH, $Cs_2CO_3$, $NaHCO_3$, $CsHCO_3$, SrO and BaO.

The reaction is preferably carried out between 230 and 260° C.

The benzotriazole derivatives according to formula (1) represent the UV chromophore moiety of the present ultraviolet radiation absorbing composition.

Most preferred compounds are Benzenepropanoic acid, 3-(2H-benzotriazol-2-yl)-5-(1,1-dimethylethyl)-4-hydroxy—, methyl ester corresponding to formula

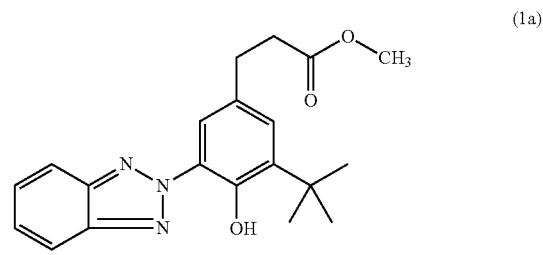 [SMILES: COC(=O)CCc1cc(-n2nc3ccccc3n2)c(O)c(C(C)(C)C)c1]

(1a)

(CAS Registry Number 84268-33-7); and

Benzenepropanoic acid, 3-(2H-benzotriazol-2-yl)-5-(1,1-dimethylethyl)-4-hydroxy-corresponding to formula

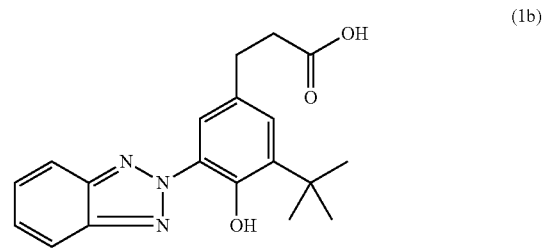 [SMILES: CC(C)(C)c1cc(CCC(=O)O)cc(-n2nc3ccccc3n2)c1O]

(1b)

(CAS Registry Number 84268-36-0).

The polymeric reaction product is composed of a complex combination of different molecules (complex reaction product).

This is further illustrated in formula (3a) representing a polymeric UV absorber according to the present invention based on a polyglycerol backbone containing 5 glycerol units (examples without limitation):

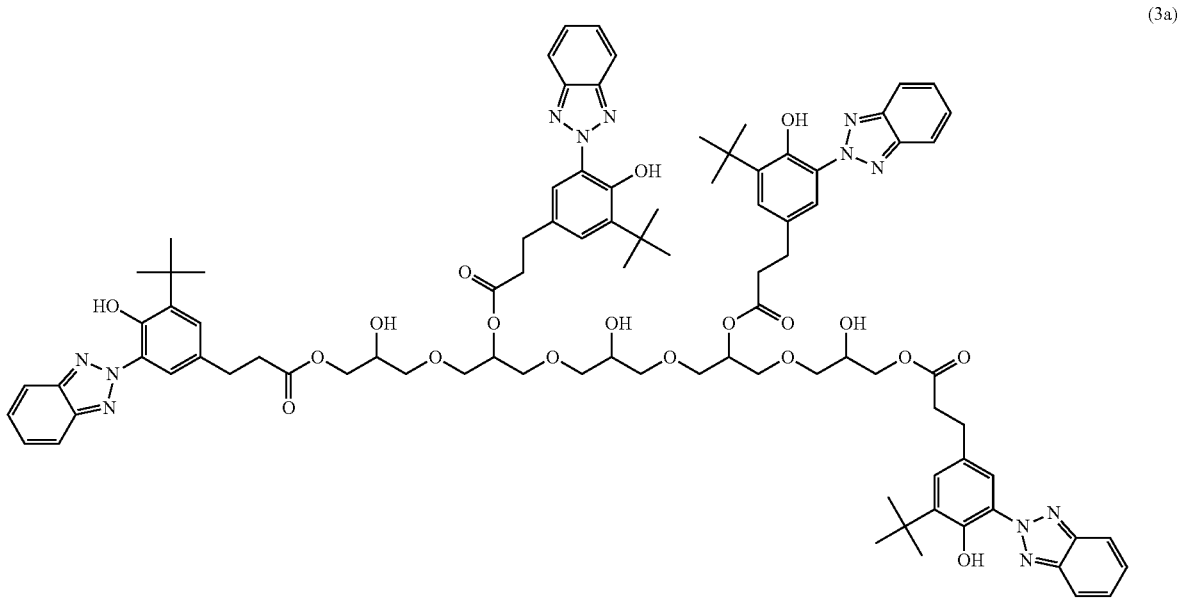 [SMILES: CC(C)(C)c1cc(CCC(=O)OCC(O)COCC(COCC(O)COCC(COCC(O)COC(=O)CCc2cc(-n3nc4ccccc4n3)c(O)c(C(C)(C)C)c2)OC(=O)CCc2cc(-n3nc4ccccc4n3)c(O)c(C(C)(C)C)c2)OC(=O)CCc2cc(-n3nc4ccccc4n3)c(O)c(C(C)(C)C)c2)cc(-n2nc3ccccc3n2)c1O]

(3a)

The glycerol backbone typically consists mainly of 3 to 10 glycerol units, whereby the hydroxyl groups of the glycerol backbone are covalently linked to the benzotriazole UV chromophore. It might be reasonably assumed, that primary hydroxyl groups (terminal units) react faster than secondary hydroxyl groups, which are less reactive for derivatization. Therefore, some secondary hydroxyl groups remain unreacted. The glycerol backbone consists of primarily linear and unbranched structure units. Branched isomers and higher molecular fractions including more than 10 glycerol units can be present.

Minor components e.g. Benzotriazole conjugates of cyclic glycerol oligomers (examples without limitation):

The polymer composition comprising the compound of formula (3) is characterized as follows:

| MW distribution | Mn > 500 Da, Mw > 1200 Da (GPC, calibrated on polystyrene) |
| --- | --- |
| Benzenepropanoic acid, 3-(2H-benzotriazol-2-yl)-5-(1,1-dimethylethyl)-4-hydroxy-, methyl ester: | ≤1.0% (HPLC) |
| Benzenepropanoic acid, 3-(2H-benzotriazol-2-yl)-5-(1,1-dimethylethyl)-4-hydroxy- | ≤1.0% (HPLC) |
| Sum of concentration of Benzenepropanoic acid, 3-(2H-benzotriazol-2-yl)-5-(1,1-dimethylethyl)-4-hydroxy-, methyl ester and Benzenepropanoic acid, 3-(2H-benzotriazol-2-yl)-5-(1,1-dimethylethyl)-4-hydroxy-: | ≤1.0% (HPLC) |

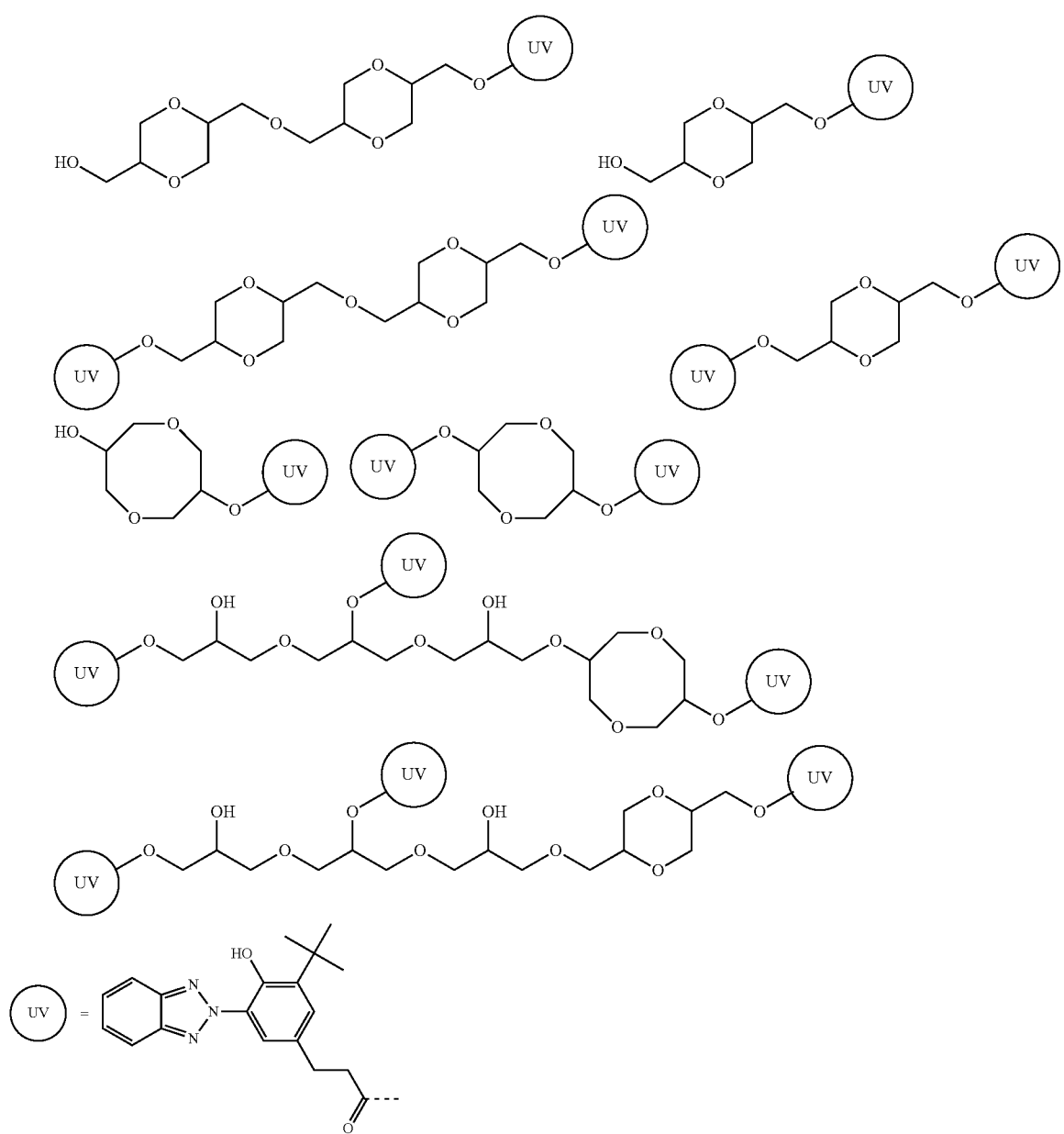

|  |  |
| --- | --- |
| MW distribution | Mn > 500 Da, Mw > 1200 Da (GPC, calibrated on polystyrene) |
| UV-absorption: | E 1% 1 cm (344 nm): >310 |
| Amount of bound chromophores: | >70% |
| Tg (° C.): | >50 (DSC) |

The characterization of the polymer composition is carried out according to the chapter "Methods" below.

Residual catalyst from transesterification reaction (Tin-II-ethyl hexanoate) <700 ppm or essentially free of Sn (IPC)
Solubility in Cetiol B: >30%
Solubility in Cetiol AB: >30%

In a preferred method of the present invention the water or alcohol which is formed during the reaction is removed by distillation during the esterification/transesterification reaction.

In a further preferred method of the present invention the esterification/transesterification is carried out at a temperature of 160-270° C., more preferably at a temperature of 190-260° C.

In a further preferred method of the present invention the esterification/transesterification is carried out without any additional solvent.

In a further preferred method of the present invention the esterification/transesterification is carried out without additional esterification/transesterification catalysts.

In a further preferred method of the present invention the esterification/transesterification is carried out under intermittent or constant vacuum of less than 250 mbar, more preferably of less than 100 mbar.

In a further preferred method of the present invention the esterification/transesterification is carried out at a temperature of 190-260 ° C. for at least 26 h.

In a further preferred method of the present invention the polyglycerol contains less than 5% of glycerol or linear and cyclic diglycerols.

In a further preferred method of the present invention the hydroxyl value of polyglycerol is in the range between 700 and 1100, more preferably between 750 and 900.

In a further preferred method of the present invention the UV chromophore is benzene propanoic acid, 3-(2H-benzotriazol-2-yl)-5-(1,1-dimethylethyl)-4-hydroxy— corresponding to formula (1b).

In a further preferred method of the present invention the UV chromophore is Benzenepropanoic acid, 3-(2H-benzotriazol-2-yl)-5-(1,1-dimethylethyl)-4-hydroxy—, methyl ester corresponding to formula (1a).

In a further preferred method of the present invention the final reaction product is used without further purification.

In a further preferred method of the present invention 1 part of polyglycerol is reacted with 2.8-3.2 parts of Benzene propanoic acid, 3-(2H-benzotriazol-2-yl)-5-(1,1-dimethylethyl)-4-hydroxy—, methyl ester corresponding to formula (1a).

In another preferred method of the present invention 1 part of polyglycerol is reacted with 2.8-3.2 parts of Benzene propanoic acid, 3-(2H-benzotriazol-2-yl)-5-(1,1-dimethylethyl)-4-hydroxy— corresponding to formula (1b).

Ultraviolet radiation absorbing polymer compositions comprising the polymer compound of formula (3) according to the present invention are especially useful as sunscreen actives for the protection of organic materials that are sensitive to ultraviolet light, especially human and animal skin and hair, against the action of UV radiation. Such UV filters are therefore suitable as light-protective agents in cosmetic and pharmaceutical applications.

A typical cosmetic or pharmaceutical composition according to the present invention comprises from 0.1 to 50% by weight, preferably from 0.5 to 20% by weight, based on the total weight of the composition , of the ultraviolet radiation absorbing polymer composition comprising the polymer compound of formula (3) according to the present invention and a cosmetically tolerable adjuvant.

The cosmetic composition according to the present invention can be prepared by physically mixing the the ultraviolet radiation absorbing polymer composition with the adjuvant using customary methods, for example by simply stirring together the individual components, especially by making use of the dissolution properties of already known cosmetic UV absorbers, for example Ethylhexyl Methoxycinnamate. The UV absorbers can be used, for example, without further treatment.

In addition to other properties, the cosmetic composition according to the present invention can be used as a radical scavenger by reducing significantly the number of UV-induced free radicals in skin when applied in a suitable cosmetic carrier.

The cosmetic composition may comprise, in addition to the ultraviolet radiation absorbing polymer composition according to the present invention, one or more further UV protective agents.

Therefore, the present invention relates to a cosmetic composition comprising a UV filter combination of
(a) a UV radiation absorbing polyglycerol benzotriazole conjugate of formula (3);
(b) UV filters selected from
($b_1$) an aqueous dispersion of 5,6,5',6'-tetraphenyl-3,3'-(1,4-Phenylene)bis(1,2,4-Triazine) corresponding to the formula

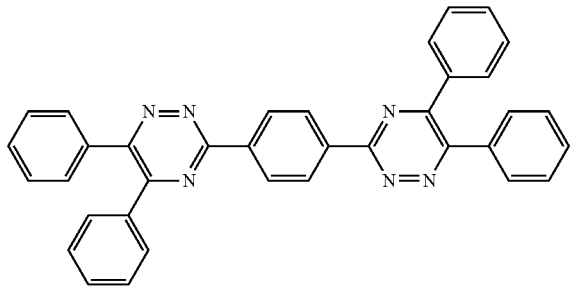

(UV-AD-1)

in particulate form; and
($b_2$) Bis-Ethylhexyloxyphenol Methoxyphenyl Triazine;
($b_3$) Butyl Methoxydibenzoylmethane;
($b_4$) Diethylhexyl Butamido Triazone;
($b_5$) Ethylhexyl Triazone;
($b_6$) Diethylamino Hydroxy Benzoyl Hexyl Benzoate;
($b_7$) Ethylhexyl Methoxycinnamate;
($b_8$) Ethylhexyl Salicylate;
($b_9$) Homosalate;
($b_{10}$) Octocrylene;
($b_{11}$) Methylene Bis-Benzotriazolyl Tetramethylbutylphenol;
($b_{12}$) Phenylbenzimidazole Sulfonic Acid;

($b_{13}$) Titanium Dioxide;

($b_{14}$) Tris-Biphenyl Triazine;

($b_{15}$) (2-{4-[2-(4-Diethylamino-2-hydroxy-benzoyl)-benzoyl]-piperazine-1-carbonyl}-phenyl)-(4-diethylamino-2-hydroxy-phenyl)-methanone;

($b_{16}$) BBDAPT; Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis—, dibutyl ester;

($b_{17}$) benzylidene malonates;

($b_{18}$) merocyanine derivatives;

($b_{19}$) Bis(butylbenzoate) diaminotriazine aminopropylsiloxane;

($b_{20}$) Bis-Ethylhexyloxyphenol Methoxyphenyl Triazine) encapsulated in a polymer matrix;

($b_{21}$) 2-(2H-Benzotriazol-2-yl)-6-[(2-ethylhexyloxy)methyl]-4-methylphenol; and ($b_{22}$) 2-Propenoic acid, 3-(4-methoxyphenyl)—, 2-methylphenyl ester; and ($b_{23}$) Zinc oxide.

wherein said composition contains at least one of the UV filters ($b_1$)-($b_{23}$); and wherein said composition also contains a pharmaceutically or cosmetically acceptable excipient.

Tinosorb S, Bis-Ethylhexyloxyphenol Methoxyphenyl Triazine encapsulated in a polymer matrix ($b_{20}$) is described in IP.com Journal (2009), 9(1B), 17 (Tinosorb S Aqua, BASF).

2-(2H-Benzotriazol-2-yl)-6-[(2-ethylhexyloxy)methyl]-4-methylphenol ($b_{21}$) corresponds to formula

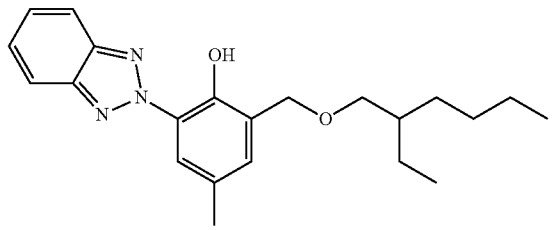
(UV-AD-2)

2-Propenoic acid, 3-(4-methoxyphenyl)—, 2-methylphenyl ester ($b_{22}$) corresponds to formula

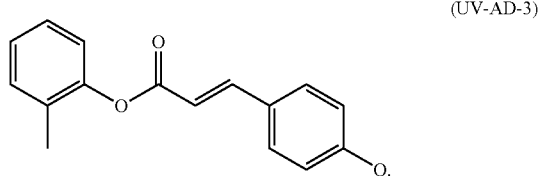
(UV-AD-3)

Preferably the UV filters ($b_{11}$) Methylene Bis-Benzotriazolyl Tetramethylbutylphenol, ($b_{14}$) Tris-Biphenyl Triazine and ($b_{15}$) (2-{4-[2-(4-Diethylamino-2-hydroxy-benzoyl)-benzoyl]-piperazine-1-carbonyl}-phenyl)-(4-diethylamino-2-hydroxy-phenyl)-methanone are present in the cosmetic or pharmaceutical composition in their micronized state.

The Benzylidene malonates ($b_{17}$) preferably correspond to formula

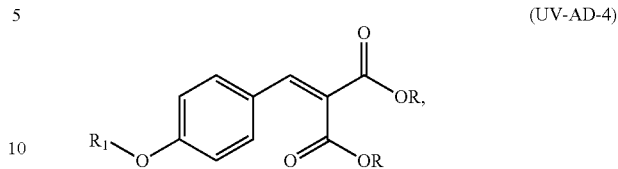
(UV-AD-4)

wherein
$R_1$ is methyl; ethyl; propyl; or n-butyl;
if $R_1$ is methyl, then R is tert. butyl;

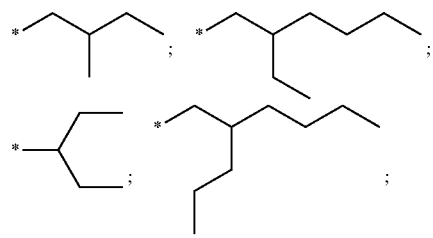

a radical of formula (UV-AD-4a)

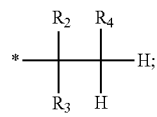

or a radical of formula (UV-AD-4b)

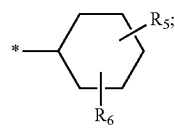

wherein
$R_2$ and $R_3$, independently from each other are hydrogen; or methyl;
$R_4$ is methyl; ethyl; or n-propyl;
$R_5$ and $R_6$ independently from each other are hydrogen; or $C_1$-$C_3$alkyl;
if $R_1$ is ethyl; propyl; or n-butyl, then R is isopropyl.

Most preferred benzylidene malonates ($b_{17}$) is the compound of formula

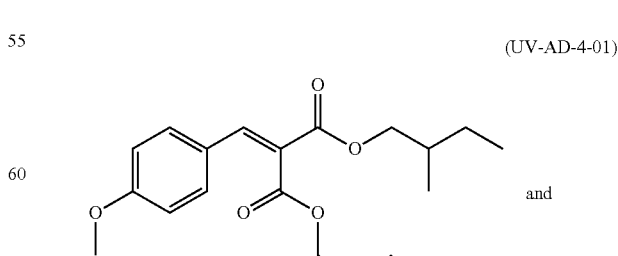
(UV-AD-4-01)

and (UV-AD-4-02)

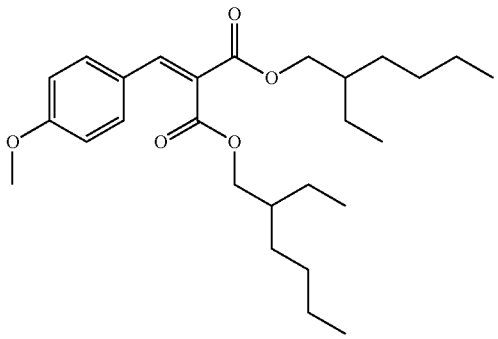

The Benzylidene malonates ($b_{17}$) and their use as UV filter in sunscreens are disclosed in detail in WO2010/136360 and WO2011/003774.

The cosmetic composition according to the present invention may comprise, in addition to the UV absorber combination according to the invention, one or more further UV protective agents of the following substance classes:

p-aminobenzoic acid derivatives, salicylic acid derivatives, benzophenone derivatives, 3-imidazol-4-yl acrylic acid and esters; benzofuran derivatives, polymeric UV absorbers, camphor derivatives, encapsulated UV absorbers, and 4,4-diphenyl-1,3-butadiene derivatives.

Special preference is given to the light-protective agents indicated in the following Table 3:

TABLE 3

Suitable UV filter substances and adjuvants which can be additionally used with the UV absorber Phenylene Bis-Diphenyltriazine according to the present invention

| Chemical Name | CAS No. |
| --- | --- |
| (+/−)-1,7,7-trimethyl-3-[(4-methylphenyl)methylene]bicyclo-[2.2.1]heptan-2-one; p-methyl benzylidene camphor | 36861-47-9 |
| 1,7,7-trimethyl-3-(phenylmethylene)bicyclo[2.2.1]heptan-2-one; benzylidene camphor | 15087-24-8 |
| (2-Hydroxy-4-methoxyphenyl)(4-methylphenyl)methanone | 1641-17-4 |
| 2,4-dihydroxybenzophenone | 131-56-6 |
| 2,2',4,4'-tetrahydroxybenzophenone | 131-55-5 |
| 2-Hydroxy-4-methoxy benzophenone; | 131-57-7 |
| 2,2'-dihydroxy-4,4'-dimethoxybenzophenone | 131-54-4 |
| 2,2'-Dihydroxy-4-methoxybenzophenone | 131-53-3 |
| Alpha-(2-oxoborn-3-ylidene)toluene-4-sulphonic acid and its salts (Mexoryl SL) | 56039-58-8 |
| Methyl N,N,N-trimethyl-4-[(4,7,7-trimethyl-3-oxobicyclo[2,2,1]hept-2-ylidene)methyl]anilinium sulphate (Mexoryl SO) | 52793-97-2 |
| Isopentyl p-methoxycinnamate; isoamyl methoxy cinnamate | 71617-10-2 |
| Menthyl-o-aminobenzoate | 134-09-8 |
| Menthyl salicylate | 89-46-3 |
| 4-aminobenzoic acid | 150-13-0 |
| Benzoic acid, 4-amino-, ethyl ester, polymer with oxirane | 113010-52-9 |
| 2-Propenamide, N-[[4-[(4,7,7-trimethyl-3-oxobicyclo[2.2.1]hept-2-ylidene)methyl]phenyl]methyl]-, homopolymer | 147897-12-9 |
| Triethanolamine salicylate | 2174-16-5 |
| 3,3'-(1,4-phenylenedimethylene)bis[7,7-dimethyl-2-oxo-bicyclo[2.2.1]heptane-1 methanesulfonic acid] (Cibafast H) | 90457-82-2 |
| Zinc oxide (primary particle size 20-100 nm) For example Zinc oxide NDM, Zinc oxide Z-Cote HP1, Nanox Zinc oxide | 1314-13-2 |
| Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester; diethylhexyl butamido triazone (Uvasorb HEB) | 154702-15-5 |
| Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane (Mexoryl XL) | 155633-54-8 |
| Dimethicodiethylbenzalmalonate; Polysilicone 15 (Parsol SLX) | 207574-74-1 |
| Benzenesulfonic acid, 3-(2H-benzotriazol-2-yl)-4-hydroxy-5-(1-methylpropyl)-, monosodium salt (Tinogard HS) | 92484-48-5 |
| 1-Dodecanaminium, N-[3-[[4-(dimethylamino)benzoyl]amino]propyl]-N,N-dimethyl-, salt with 4-methylbenzenesulfonic acid (1:1) (Escalol HP610) | 156679-41-3 |
| 1-Propanaminium, N,N,N-trimethyl-3-[(1-oxo-3-phenyl-2-propenyl)-amino]-, chloride | 177190-98-6 |
| 1H-Benzimidazole-4,6-disulfonic acid, 2,2'-(1,4-phenylene)bis- | 170864-82-1 |
| 1,3,5-Triazine, 2,4,6-tris(4-methoxyphenyl)- | 7753-12-0 |
| 1,3,5-Triazine, 2,4,6-tris[4-[(2-ethylhexyl)oxy]phenyl]- | 208114-14-1 |
| 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 2-Propenoic acid, 3-(1H-imidazol-4-yl)- | 104-98-3 |
| Benzoic acid, 2-hydroxy-, [4-(1-methylethyl)phenyl]methyl ester | 94134-93-7 |
| 1,2,3-Propanetriol, 1-(4-aminobenzoate) (Glyceryl PABA) | 136-44-7 |
| Benzeneacetic acid, 3,4-dimethoxy-a-oxo- | 4732-70-1 |
| 2-Propenoic acid, 2-cyano-3,3-diphenyl-, ethyl ester | 5232-99-5 |
| Anthralinic acid, p-menth-3-yl ester | 134-09-8 |

TABLE 3-continued

Suitable UV filter substances and adjuvants which can be additionally used with the UV absorber Phenylene Bis-Diphenyltriazine according to the present invention

| Chemical Name | CAS No. |
| --- | --- |
| 2,2'-bis(1,4-phenylene)-1H-benzimidazole-4,6-disulphonic acid mono sodium salt or Disodium phenyl dibenzimidazole tetrasulfonate (Neo Heliopan AP) | 349580-12-7 |
| sterols (cholesterol, lanosterol, phytosterols), as described in WO0341675 | |
| mycosporines and/or mycosporine-like amino acids as described in WO2002039974, e.g. Helioguard 365 from Milbelle AG, isolated mycosporine like amino acids from the red alga *porphyra umbilicalis* (INCI: *Porphyra Umbilicalis*) that are encapsulated into liposomes) | |
| alpha-lipoic-acid as described in DE 10229995 | |
| synthetic organic polymers as described in EP 1 371 358, [0033]-[0041] | |
| phyllosilicates as described in EP 1371357 [0034]-[0037] | |
| silica compounds as described in EP1371356, [0033]-[0041] | |
| inorganic particles as described in DE10138496 [0043]-[0055] | |
| latex particles as described in DE10138496 [0027]-[0040] | |
| 1H-Benzimidazole-4,6-disulfonic acid, 2,2'-(1,4-phenylene)bis-, disodium salt; Bisimidazylate (Neo Heliopan APC) | 180898-37-7 |
| Di-2-ethylhexyl-3,5-dimethoxy-4-hydroxy-benzalmalonate (Oxynex ST, EMD Chemicals, as described in US 20040247536) | |
| Z-COTE ® MAX: Zinc Oxide (and) Diphenyl Capryl Methicone | |
| Z-COTE HP1: Zinc Oxide (and) Triethoxycaprylylsilane | |
| 1,3,5-Triazine-2,4,6-triamine, N2,N4-bis[4-[5-(1,1-dimethylpropyl)-2-benzoxazolyl]phenyl]-N6-(2-ethylhexyl)- (Uvasorb K2A) | 288254-16-0 |
| 1,1-[(2,2'-Dimethylpropoxy)carbonyl]-4,4-diphenyl-1,3-butadiene | 363602-15-7 |
| UV filter capsules containing an organic sunscreen as described in DE102007035567 or WO 2009012871 | |

If the compositions according to the present invention represent water- and oil-containing emulsions (e.g. W/O, O/W, O/W/O and W/O/W emulsions or microemulsions) they contain, for example, from 0.1 to 30% by weight, preferably from 0.1 to 15% by weight and especially from 0.5 to 10% by weight, based on the total weight of the composition, of the ultraviolet radiation absorbing polymer compound of formula (3), from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically tolerable adjuvants.

Suitable oil components of oil-containing compositions (e.g. oils, W/O, O/W, O/W/O and W/O/W emulsions or microemulsions) are for example Guerbet alcohols based on fatty alcohols having from 6 to 18, preferably from 8 to 10, carbon atoms, esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, triglycerides based on $C_6$-$C_{10}$ fatty acids, liquid mono-/di-/tri-glyceride mixtures based on $C_6$-$C_{18}$ fatty acids, esters of $C_6$-$C_{24}$ fatty alcohols and/or Guerbet alcohols with aromatic carboxylic acids, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups, vegetable oils (such as sunflower oil, olive oil, soy-bean oil, rapeseed oil, almond oil, jojoba oil, orange oil, wheat germ oil, peach kernel oil and the liquid components of coconut oil), branched primary alcohols, substituted cyclohexanes, linear and branched $C_6$-$C_{22}$ fatty alcohol carbonates, Guerbet carbonates, esters of benzoic acid with linear and/or branched $C_6$-$C_{22}$ alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyldecyl ether, tert-butyl n-octyl ether, isopentyl n-octyl ether and 2-methyl pentyl-n-octyl ether; ring-opening products of epoxidised fatty acid esters with polyols, silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols). Of special importance are isopropyl myristate, isononanoic acid $C_{16}$-$C_{18}$alkyl esters, stearic acid 2-ethylhexyl ester, cetyl oleate, glycerol tricaprylate, coconut fatty alcohol caprinate/caprylate and n-butyl stearate. Further oil components that can be used are dicarboxylic acid esters, such as di-n-butyl adipate, di(2-ethylhexyl) adipate, di(2-ethylhexyl) succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or trivalent metal salts (alkaline earth metal, $Al^{3+}$ inter alia) of one or more alkyl carboxylic acids.

The oil components can be used in an amount of, for example, from 1 to 60% by weight, especially from 5 to 50% by weight and preferably from 10 to 35% by weight, based on the total weight of the composition.

Any conventionally emulsifier can be used for the cosmetic compositions according to the present invention.

Suitable emulsifiers are for example, non-ionic surfactants from the following groups:
  addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;
  $C_{12}$-$C_{22}$ fatty acid mono- and di-esters of addition products of from 1 to 30 mol of ethylene oxide with polyols having from 3 to 6 carbon atoms, especially with glycerol;
  glycerol mono- and di-esters and sorbitan mono- and di-esters of saturated and unsaturated fatty acids having from 6 to 22 carbon atoms and ethylene oxide addition products thereof, for example glyceryl stearates, glyceryl isostearates, glyceryl oleates, sorbitan oleates or sorbitan sesquioleates;
  $C_8$-$C_{22}$alkyl-mono- and -oligo-glycosides and ethoxylated analogues thereof, degrees of oligomerisation of from 1.1 to 5, especially from 1.2 to 1.4, being preferred, and glucose being preferred as the sugar component;
  addition products of from 2 to 60 mol, especially from 15 to 60 mol, of ethylene oxide with castor oil and/or hydrogenated castor oil;
  polyol esters and especially polyglycerol esters, for example diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable;
  partial esters based on linear, branched, unsaturated or saturated $C_6$-$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearates or polyglyceryl-2-diricinoleates;
  mono-, di- and tri-alkylphosphates and also mono-, di- and/or tri-PEG-alkylphosphates and salts thereof;
  wool wax alcohols;
  one or more ethoxylated esters of natural derivatives, for example polyethoxylated esters of hydrogenated castor oil;
  silicone oil emulsifiers, for example silicone polyol;
  polysiloxane/polyalkyl/polyether copolymers and corresponding derivatives, for example cetyl dimethicone copolyol;
  mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearates, polyglyceryl-3-glucose dioleates, methyl glucose dioleates or dicocoyl pentaerythryl distearyl citrates; and also
  polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$-$C_{18}$ fatty acid mono- and di-esters of addition products of ethylene oxide with glycerol are known, for example, from DE-A-2 024 051 as fat-restoring substances for cosmetic preparations.

$C_8$-$C_{18}$Alkyl-mono- and -oligo-glycosides, their preparation and their use are known from the prior art. They are prepared especially by reacting glucose or oligosaccharides with primary alcohols having from 8 to 18 carbon atoms. Suitable glycoside radicals include monoglycol-sides in which a cyclic sugar radical is glycosidically bonded to the fatty alcohol and also oligomeric glycosides having a degree of oligomerization of up to preferably about 8. The degree of oligomerization is a statistical average value based on a homologue distribution customary for such technical-grade products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethyl-imidazolines each having from 8 to 18 carbon atoms in the alkyl or acyl group and also cocoacylaminoethylhydroxyethylcarboxymethylglycinate. Special preference is given to the fatty acid amide derivative known by the CTFA name cocamidopropyl betaine. Likewise suitable as emulsifiers are ampholytic surfactants. Ampholytic surfactants are to be understood as meaning especially those which, in addition to containing a $C_8$-$C_{18}$-alkyl or -acyl group, contain at least one free amino group and at least one —COOH or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkyl-sarcosines, 2-alkylaminopropionic acids and alkylaminoacetic acids, each having approximately from 8 to 18 carbon atoms in the alkyl group.

Ampholytic surfactants to which special preference is given are N-cocoalkylamino-propionate, cocoacylaminoethylaminopropionate and $C_{12}$-$C_{18}$acylsarcosine. In addition to the ampholytic emulsifiers there also come into consideration quaternary emulsifiers, special preference is given to those of the esterquat type, preferably methyl-quaternised di-fatty acid triethanolamine ester salts.

Non-ionic emulsifiers are preferred, preferably ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The compositions according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, antioxidants, hydrotropic agents, preservatives, insect repellents, self-tanning agents, solubilizers, perfume oils, colorants, bacteria-inhibiting agents and the like.

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensation products, the latter preferably being based on wheat proteins.

Suitable pearlescent are for example: alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Suitable consistency regulators are especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methylglucamides of identical chain length and/or polyglycerol poly-12-hydroxystearates. Suitable thickeners include, for example, Aerosil types (hydrophilic silicic acids), polysaccharides, especially xanthan gum, guar-guar, agar-agar, alginates and Tyloses, carboxymethyl cellulose and hydroxymethyl cellulose, also relatively high molecular weight polyethylene glycol mono- and di-esters of fatty acids, polyacrylates (e.g. Carbopol® from Goodrich or Synthalen® from Sigma), polyacrylamides, polyvinyl alcohol and polyvinylpyrrolidone, surfactants, for example ethoxylated fatty acid glycerides, esters of fatty acids with polyols, for example pentaerythritol or trimethyloipropane, fatty alcohol ethoxylates with restricted homologue distribution and alkyloligoglucosides as well as electrolytes, such as sodium chloride or ammonium chloride.

Suitable cationic polymers are, for example, cationic cellulose derivatives, for example a quaternised hydroxymethyl cellulose obtainable under the name Polymer JR 400® from Amerchol, cationic starch, copolymers of diallylammonium salts and acrylamides, quaternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat®L/Grünau), quaternised wheat polypeptides, polyethyleneimine, cationic silicone polymers, for example amidomethicones, copolymers of adipic acid and dimethylaminohydroxypropyldiethylenetriamine (Cartaretin®/Sandoz), copolymers of acrylic acid with dimethyldiallylammonium chloride (Merquat® 550/Chemviron), polyaminopolyamides, as described, for example, in FR-A-2 252 840, and the crosslinked water-soluble polymers thereof, cationic chitin derivatives, for example quaternised chitosan, optionally distributed as microcrystals; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol.

Suitable anionic, zwitterionic, amphoteric and non-ionic polymers are for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones.

Suitable silicone compounds are, for example, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Typical examples of fats are glycerides, and as waxes there come into consideration, inter alia, beeswax, carnauba wax, candelilla wax, montan wax, paraffin wax, hydrogenated castor oils and fatty acid esters or microwaxes solid at room temperature optionally in combination with hydrophilic waxes, e.g. cetylstearyl alcohol or partial glycerides. Metal salts of fatty acids, for example magnesium, aluminium and/or zinc stearate or ricinoleate, may be used as stabilizers.

Biogenic active ingredients are for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizing active ingredients are for example, antiperspirants like aluminium chlorohydrates (see J. Soc. Cosm. Chem. 24, 281 (1973)). Aluminium chlorohydrate corresponding to formula $Al_2(OH)_5Cl \times 2.5\ H_2O$, known and commercially available under the trade mark Locron® of Hoechst AG, Frankfurt (FRG), is especially preferred (see J. Pharm. Pharmacol. 26, 531 (1975)). Beside the chlorohydrates, it is also possible to use aluminium hydroxy-acetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/FRG), which inhibit enzyme activity and hence reduce odour formation. Further suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the microbial flora and kill, or inhibit the growth of, sweat-decomposing bacteria can likewise be present in the preparations (especially in stick preparations). Examples include chitosan, phenoxyethanol and chlorhexidine gluconate. 5-Chloro-2-(2,4-dichlorophenoxy)-phenol (Irgasan®, BASF has also proved especially effective.

Suitable anti-dandruff agents are for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds. Suitable swelling agents for aqueous phases are montmorillonites, clay mineral substances, Pemulen and also alkyl-modified types of Carbopol (Goodrich). Further suitable polymers and swelling agents can be found in the review by R. Lochhead in Cosm. Toil. 108, 95 (1993).

In addition to the primary light-protective substances it is also possible to use secondary light-protective substances of the antioxidant type which interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine) in very small tolerable amounts (e.g. from pmol to µmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, butyl hydroxyanisole, resinous nordihydroguaiaretic acid, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the sodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 to 30% by weight, preferably from 0.01 to 3% by weight, based on the weight of the cosmetic composition according to the present invention.

For improvement of the flow behavior it is also possible to employ hydrotropic agents, for example ethanol, isopropyl alcohol or polyols. Suitable polyols for that purpose comprise preferably from 2 to 15 carbon atoms and at least two hydroxy groups.

The polyols may also contain further functional groups, especially amino groups, and/or may be modified with nitrogen. Typical examples are as follows:

glycerol;

alkylene glycols, for example ethylene glycol, diethylene glycol, propylene glycol, butylene glycol, hexylene glycol and also polyethylene glycols having an average molecular weight of from 100 to 1000 dalton;

technical oligoglycerol mixtures having an intrinsic degree of condensation of from 1.5 to 10, for example technical diglycerol mixtures having a diglycerol content of from 40 to 50% by weight;

methylol compounds, such as, especially, trimethylolethane, trimethylolpropane, trimethyl-olbutane, pentaerythritol and dipentaerythritol;

lower alkyl-glucosides, especially those having from 1 to 8 carbon atoms in the alkyl radical, for example methyl and butyl glucoside;

sugar alcohols having from 5 to 12 carbon atoms, for example sorbitol or mannitol;

sugars having from 5 to 12 carbon atoms, for example glucose or saccharose;

amino sugars, for example glucamine;

dialcohol amines, such as diethanolamine or 2-amino-1,3-propanediol.

Suitable preservatives include, for example, phenoxyethanol, formaldehyde solution, Parabens, pentanediol or sorbic acid and the further substance classes listed in Schedule 6, Parts A and B of the Cosmetics Regulations.

Suitable perfume oils are mixtures of natural and/or synthetic aromatic substances. Representatives of natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type.

Aromatic substance compounds of the ester type are, for example, benzyl acetate, phenoxyethyl isobutyrate, p-tert-butylcyclohexyl acetate, linalyl acetate, dimethyl-benzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, a-hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, β-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

As colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106 may be used. The colourants are usually used in concentrations of from 0.001 to 0.1% by weight, based on the total mixture.

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide).

A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the cosmetic composition according to the present invention.

The cosmetic compositions according to the present invention may furthermore contain as adjuvants anti-foams, such as silicones, structurants, such as maleic acid, solubilizers, such as ethylene glycol, propylene glycol, glycerol or diethylene glycol, opacifiers, such as latex, styrene/PVP or styrene/acrylamide copolymers, complexing agents, such as EDTA, NTA, β-alaninediacetic acid or phosphonic acids, propellants, such as propane/butane mixtures, $N_2O$, dimethyl ether, $CO_2$, $N_2$ or air, so-called coupler and developer components as oxidation dye precursors, thioglycolic acid and derivatives thereof, thiolactic acid, cysteamine, thiomalic acid or α-mercaptoethanesulfonic acid as reducing agents or hydrogen peroxide, potassium bromate or sodium bromate as oxidizing agents.

Insect repellents are for example, N,N-diethyl-m-toluamide, 1,2-pentanediol or insect repellent 3535.

Suitable self-tanning agents are dihydroxyacetone, erythrulose or mixtures of dihydroxyacetone and erythrulose.

Cosmetic formulations according to the invention are contained in a wide variety of cosmetic preparations, especially the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and anti-perspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, parfume), parfume oils or parfume creams;

cosmetic hair-treatment preparations, e.g. hair-washing preparations in the form of shampoos and conditioners, hair-care preparations, e.g. pre-treatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The final formulations may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Important cosmetic compositions for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milks and sun protection preparations in the form of a spray.

Important cosmetic compositions for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition:
0.01 to 5% by weight of a UV absorber composition according to the invention,
12.0% by weight of sodium laureth-2-sulfate,
4.0% by weight of cocamidopropyl betaine,
3.0% by weight of sodium chloride, and
water ad 100%.

Especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl-dimethyl-2-hydroxyethylammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl-dimethyl-2-hydroxyethylammonium chloride or Quaternium 80 is added;

b) Quat-doped solutions of the UV absorber according to the invention in butyltriglycol and tributyl citrate;

c) mixtures or solutions of the UV absorber according to the invention with n-alkylpyrrolidone.

The following examples are illustrative of the principles and practice of the present invention, although not limited thereto.

Methods

Determination of 3-(2H-benzotriazol-2-yl)-5-(1,1-dimethylethyl)-4-hydroxy-benzenepropanoic acid and 3-(2H-benzotriazol-2-yl)-5-(1,1-dimethylethyl)-4-hydroxy-benzenepropanoic acid methyl ester by HPLC Operation range: The concentration of both compounds can be determined from 0.02% -10% w/w %.

Solvents: Water HPLC-quality, acetonitrile HPLC-quality, tetrahydrofurane HPLC-quality, tetrabutyl ammonium hydrogensulfate (TBAHS) HPLC-quality Column: Eclipse XDB C8 4.6*150 mm 5 µm
Mobile phase A: Water—acetonitrile 9:1+TBAHS 2 g/l
Mobile phase B: Acetonitrile—tetrahydrofurane 1:1
Flow: 1.1 ml/min
Injection volume: 10 µl
Oven temperature: 50° C.
Detection wavelength: 302 nm

| Gradient | Time [min] | A [%] | B [%] |
|---|---|---|---|
|  | 0 | 50 | 50 |
|  | 15 | 2 | 98 |
|  | 20 | 2 | 98 |
|  | 21 | 50 | 50 |
| Post Time | 5 |  |  |

Calibration: The quantification is carried by means of a single point calibration. About 10 mg of acid ester is weighted in a 100 ml brown volumetric flask and filled up with tetrahydrofurane. The sample is dissolved in an ultrasonic bath for about 5 min and the solution is analyzed. This solution is diluted 1:10 with THF.

Hydrolysis of Ultraviolet Radiation Absorbing Compositions 100 mg of the ultraviolet radiation absorbing composition is dissolved in 100 ml of a solvent mixture (70 parts THF/30 parts 0.1N NaOH) and 2-3 drops of water are added. The sample must be completely dissolved, otherwise a few drops of water have to be added. The mixture is heated at 50° C. for 2 h in a drying cabinet. After cooling to room temperature, 1 ml of this solution is transferred to a 100 ml volumetric flask and filled up with THF. The content of 3-(2H-benzotriazol-2-yl)-5-(1,1-dimethylethyl)-4-hydroxy-benzenepropanoic acid is analyzed by HPLC.

Amount of Covalently Bound Chromophore:

The amount of chromophore is calculated as w/w % of 3-(2H-benzotriazol-2-yl)-5-(1,1-dimethylethyl)-4-hydroxy-benzene-propanoic acid.

The amount of covalently bound chromophore is determined as follows:

| HPLC analysis of the reaction product (determination of the unbound chromophore) | |
|---|---|
| Compound | % |
| 3-(2H-benzotriazol-2-yl)-5-(1,1-dimethylethyl)-4-hydroxy-benzene-propanoic acid methyl ester | A |
| 3-(2H-benzotriazol-2-yl)-5-(1,1-dimethylethyl)-4-hydroxy-benzene-propanoic acid | E |
| Sum | S |

| HPLC analysis of the completely hydrolyzed reaction product (determination of the unbound and bound chromophore) | |
|---|---|
| Compound | % |
| 3-(2H-benzotriazol-2-yl)-5-(1,1-dimethylethyl)-4-hydroxy-benzene-propanoic acid | C |

Amount of Covalently Bound Chromophore T (%):

$$T=C-(A+E)=C-S$$

Determination of E (1%/1 cm) at 343 nm by UV spectroscopy:

Spectrophotometer Lamda 950 S (or equivalent)
Cell Type: Quarz, 10 mm
Reference: 1.4-dioxane
Temperature: ca.25° C.
Solvent: 1.4-dioxane, spectrophotometric grade
Preparation of the test solutions: About 25 mg of sample is weighed with a precision balance into a 100.0 ml (Vs) volumetric flask. It is filled up to the mark with 1.4-dioxane. 10.0 ml (V) of this solution is diluted to 100.0 ml (Vf) with 1.4-dioxane. The absorbance of this solution is measured between 290 and 450 nm.

Calculation of E (1%/1 cm):
Weighing w=in mg
Total volume of stock solution Vs
Used volume of stock solution V
Final volume of solution Vf
Cell d=10 mm
Wavelength maximum λ=343 nm
Measured absorbance at 343 nm A $$E(1\%, 1 \text{ cm}) = A_m \cdot \frac{Vs \cdot Vf * 10}{w \cdot V}$$

Determination of methanol by headspace GC-MS
Standard: Methanol
Solvents: 1,3-Dimethyl-2-imidazolidinone=DMI
Autosampler: Agilent G 1888 Headspace
Temperature: Oven: 100° C. loop: 110° C. transfer Line: 130° C.
Shaking: High
Pressure (psi): Carrier: 17.8 Vial: 13.0
Timing (minutes) Vial Equil.: 30.0
Pressure: 3.00
Loop Fill: 0.20
Loop Equil.: 0.05
Inject: 1.00
Gas Chromatograph: Agilent 6890
Injection technique: Split, 30 ml He/min.
Column: DB-VRX, film thickness 1.4 μm, 60 m×0.25 mm
Carrier gas: He, 1.0 ml/min
Temperatures: Injector: 220° C.
Oven: 2 min 50° C.//10° C./min to 260° C.//isothermal 15 min
Detector: Agilent 5973 Inert Mass Selective detector
EM Volts: 1718
Solvent Delay: 0.00; detector off: 15.0 min
SIM Modus: Component Ions, methanol 31

A standard calibration curve is generated by plotting the concentration of methanol vs. the peak area obtained.

$$y=mx+b$$

y=peak area
m=slope
x=concentration of methanol (mg/100 ml)
b=y intercept
x (mg/100 ml)=(y−b)/m Molecular weight distribution by GPC
Method: Gel Permeation Chromatography with RI-Detection
Standards: EasiVial GPC/SEC Calibration Standards PSS Part. No: PL2010-0201 Agilent
Solvents: Tetrahydrofurane HPLC quality, diethanolamine puriss p.a.
Apparatus: Malvern Viscotek with RI-Detector
Chromatography Conditions:
Column1: PSS SDV 100,000 A, 8×300 mm, 5 u
Column2: PSS SDV 1000 A, 8×300 mm, 5 u
Oven temperature: 40° C.
Mobile Phase: Tetrahydrofurane+3.7 g/L DEA
Flow: 1.0 ml/min
Sample concentration: approx. 2 mg/ml in the same solvent mixture as the mobile phase.
Calibration: Conventional calibration homopolymeres. Polystyrene reference samples.

Gardner Color

Spectral color measurement with Lange, LICO 300; 30% solution of the ultraviolet radiation absorbing composition in dibutyl adipate (Cetiol B).

Determination of the glass transition temperature ($T_g$) by DSC

Differential Scanning calorimeter (DSC 822e, Mettler Toledo), 40 μl aluminium crucible, micro scale (MX5, Mettler Toledo). The oven is nitrogen-purged.

Procedure: 3-7 mg sample is charged with the micro scale into an aluminium crucible. The crucible is closed hermetically with an aluminium cover. Two crucibles are prepared per sample. The prepared crucible is put in the DSC equipment and the method is started as described below.

First scan: −30° C. to 200° C., 10° C./min heating rate
Second scan: Cool to −30° C. with −10° C./min cooling rate
Third scan: −30° C. to 200° C., 10° C./min heating rate The third scan is used for the determination of the glass transition temperature.

The mean of the glass transition temperature is calculated.

Determination of Sn by Inductively Coupled Plasma Atomic Emission Spectrometry (ICP-AES).

The sample preparation is done by pressurized wet digestion in PTFE vessels: About 200 mg of the sample is treated with 3 ml HNO₃ at a temperature of about 150° C. for six hours and cooled down to room temperature. The obtained solution is diluted with deionized water to an end volume of 20 ml and directly measured by ICP-AES.

The calibration is done by external standard method with commercially available elemental standard solutions. As a typical apparatus a Varian Vista Pro ICP-AES or Agilent 5100 ICP-AES spectrometer can be used. Specific wavelengths for evaluation: Sn, 189.924 nm for the quantitative evaluation as well as 133, 138, 143, 146 and 284 nm to check possible interferences.

Determination of the Solubility in Cosmetic Solvents 800 mg of pulverized UV filter is suspended in 1200 mg solvent in a glass container. A magnetic stirring bar is added. The container is closed and stirred over night at room temperature (20-30° C.). It has always to be checked that the stirrer does not stick to the glass container.

Specification: clear or slightly turbid solution

Cosmetic solvents: Dicaprylyl carbonate (Cetiol CC, BASF), C12-15 alkyl benzoate (Cetiol AB, BASF), Dibutyl adipate (Cetiol B, BASF)

EXAMPLES

Polyglycerol

Polyglycerol is prepared as described in WO 2002 036534, US 2002 0058781 and U.S. Pat. No. 6,620,904. CaO or Ca(OH)₂ is used as catalyst. Glycerol, diglycerol and other low molecular fractions are removed from the reaction product e.g. by short path distillation in order to achieve a specific quality.

Properties of polyglycerol: yellow to brown material; very high viscosity at room temperature, hydroxyl-value 800-1000, water content <0.2%, glycerol and diglycerols <5.5% (determined by GC after derivatization with a silylating agent).

Example A1

Transesterification Product of 3-(2H-benzotriazol-2-yl)-5-(1,1-dimethylethyl-4-hydroxy-benzenepropanoic Acid with Polyglycerol 3-(2H-benzotriazol-2-yl)-5-(1,1-dimethylethyl)-4-hydroxy-benzene-propanoic acid (605.8 g) is charged into a glass reactor equipped with nitrogen inlet, dephlegmator (120° C.) and agitation. The temperature is set to 227° C. in order to melt the 3-(2H-benzotriazol-2-yl)-5-(1,1-dimethylethyl)-4-hydroxy-benzene-propanoic acid. As soon as the 3-(2H-benzotriazol-2-yl)-5-(1,1-dimethylethyl)-4-hydroxy-benzene-propanoic acid is completely melted, tin-(II)-2-ethyl-hexanoate (0.48 g) is added and the reactor is evacuated to 860 mbar. Molten polyglycerol (207.1 g) is charged within 1 h, while maintaining a reaction temperature of 220-225° C. and a pressure of 30 mbar. Methanol is distilled of. Thereafter the vacuum is reduced gradually to 5-8 mbar at 225° C. and the reaction mass is stirred for 16-18 h, until the total concentration of 3-(2H-benzotriazol-2-yl)-5-(1,1-dimethylethyl)-4-hydroxy-benzene-propanoic acid methyl ester and 3-(2H-benzotriazol-2-yl)-5-(1,1-dimethylethyl)-4-hydroxy-benzene-propanoic acid is below 1.0%. The composition of the reaction mixture is monitored by HPLC. After cooling down to ambient temperature, the UV-absorbing polymer composition (756.3 g) is obtained as a yellow to amber glassy solid.

| HPLC (unbound chromophore) | |
|---|---|
| Compound | % |
| 3-(2H-benzotriazol-2-yl)-5-(1,1-dimethylethyl)-4-hydroxy-benzene-propanoic acid methyl ester | |
| 3-(2H-benzotriazol-2-yl)-5-(1,1-dimethylethyl)-4-hydroxy-benzene-propanoic acid | |
| Sum | <1% | a

| Solubility | |
|---|---|
| Solvent | % |
| C12-15 alkyl benzoate | >40 |
| Dibutyl adipate | >40 |
| Dicaprylyl carbonate | >40 |

Example A2

Ultraviolet radiation absorbing composition: Transesterification product of 3-(2H-benzotriazol-2-yl)-5-(1,1-dimethylethyl)-4-hydroxy-benzenepropanoic Acid Methyl Ester with Polyglycerol 3-(2H-benzotriazol-2-yl)-5-(1,1-dimethylethyl)-4-hydroxy-benzene-propanoic acid methyl ester (630.9 g) is charged into a glass reactor equipped with nitrogen inlet, dephlegmator (120° C.) and agitation. The temperature is set to 227° C. in order to melt the 3-(2H-benzotriazol-2-yl)-5-(1,1-dimethylethyl)-4-hydroxy-benzene-propanoic acid methyl ester. As soon as the 3-(2H-benzotriazol-2-yl)-5-(1,1-dimethylethyl)-4-hydroxy-benzene-propanoic acid methyl ester is completely melted, tin-(II)-2-ethylhexanoate (0.48 g) is added and the reactor is evacuated to 860 mbar. Molten polyglycerol (206.9 g) is charged within 1 h, while maintaining a reaction temperature of 220-225° C. and a pressure of 30 mbar. Methanol is distilled of. Thereafter the vacuum is reduced gradually to 5-8 mbar at 225° C. and the reaction mass is stirred for 16-18 h, until the total concentration of 3-(2H-benzotriazol-2-yl)-5-(1,1-dimethylethyl)-4-hydroxy-benzene-propanoic acid methyl ester and 3-(2H-benzotriazol-2-yl)-5-(1,1-dimethylethyl)-4-hydroxy-benzene-propanoic acid is below 1.0%.

The composition of the reaction mixture is monitored by HPLC. After cooling down to ambient temperature, the UV-absorbing polymer composition (750.3 g) is obtained as a yellow to amber glassy solid.

| HPLC (unbound chromophore) | |
|---|---|
| Compound | % |
| 3-(2H-benzotriazol-2-yl)-5-(1,1-dimethylethyl)-4-hydroxy-benzene-propanoic acid methyl ester | 0.2 |
| 3-(2H-benzotriazol-2-yl)-5-(1,1-dimethylethyl)-4-hydroxy-benzene-propanoic acid | 0.6 |
| Sum | 0.8 |

| UV | | | | | |
|---|---|---|---|---|---|
| Wave-length (nm) | E (1%, 1 cm) | Solubility | | GPC | |
| | | Solvent | % | Peak RV - (ml) | 18.4 |
| 344 | 336 | C12-15 alkyl benzoate | >40 | | |
| | | Dibutyl adipate | >40 | Mn - (Daltons) | 872 |
| | | Dicaprylyl carbonate | >40 | Mw - (Daltons) | 1577 |
| | | | | Mz - (Daltons) | 2370 |
| | | | | Mp - (Daltons) | 1341 |
| | | | | Mw/Mn | 1.80 |

Example A3

Ultraviolet radiation absorbing composition: Transesterification product of 3-(2H-benzotriazol-2-yl)-5-(1,1-dimethylethyl)-4-hydroxy-benzenepropanoic Acid Methyl Ester with Polyglycerol 3-(2H-benzotriazol-2-yl)-5-(1,1-dimethylethyl)-4-hydroxy-benzene-propanoic acid methyl ester (630.84 g, 1.785 mol) is charged into a glass reactor equipped with nitrogen inlet, dephlegmator (120° C.) and agitation. The temperature is set to 197° C. in order to melt the 3-(2H-benzotriazol-2-yl)-5-(1,1-dimethylethyl)-4-hydroxy-benzene-propanoic acid methyl ester. As soon as the 3-(2H-benzotriazol-2-yl)-5-(1,1-dimethylethyl)-4-hydroxy-benzene-propanoic acid methyl ester is completely melted, tin-(II)-2-ethylhexanoate (0.47 g, 1.2 mmol) is added and the reactor is evacuated to 850 mbar. Molten polyglycerol (206.3 g) is charged within 1 h, while maintaining a reaction temperature of 185-190° C. Methanol is distilled of. Thereafter the vacuum is reduced gradually to 5-8 mbar at 197° C. and the reaction mass is stirred for 48 h, until the total concentration of 3-(2H-benzotriazol-2-yl)-5-(1,1-dimethylethyl)-4-hydroxy-benzene-propanoic acid methyl ester and 3-(2H-benzotriazol-2-yl)-5-(1,1-dimethylethyl)-4-hydroxy-benzene-propanoic acid is below 1.0%. The composition of the reaction mixture is monitored by HPLC. After cooling down to ambient temperature, the UV-absorbing polymer composition (748.5 g) is obtained as a yellow to amber glassy solid.

| HPLC (unbound chromophore) | |
|---|---|
| Compound | % |
| 3-(2H-benzotriazol-2-yl)-5-(1,1-dimethylethyl)-4-hydroxy-benzene-propanoic acid methyl ester | 0.1 |
| 3-(2H-benzotriazol-2-yl)-5-(1,1-dimethylethyl)-4-hydroxy-benzene-propanoic acid | 0.5 |
| Sum | 0.6 |

| UV | | | | | |
|---|---|---|---|---|---|
| Wave-length (nm) | E (1%, 1 cm) | Solubility | | GPC | |
| | | Solvent | % | Peak RV - (ml) | 18.16 |
| 300 | 346 | C12-15 alkyl benzoate | >40 | Mn - (Daltons) | 911 |
| 320 | 284 | Dibutyl adipate | >40 | Mw - (Daltons) | 1584 |
| 340 | 342 | Dicaprylyl carbonate | >40 | Mz - (Daltons) | 2277 |
| 360 | 263 | | | Mp - (Daltons) | 1383 |
| 380 | 70 | | | Mw/Mn | 1.74 |

| UV | | | | | |
|---|---|---|---|---|---|
| Wave-length (nm) | E (1%, 1 cm) | Solubility | | GPC | |
| | | Solvent | % | Peak RV - (ml) | 18.16 |
| 400 | 1 | | | | |
| 344 | 345 | | | | |
| 343 | 345 | | | | |
| 303 | 351 | | | | |

Example A4

Ultraviolet Radiation Absorbing Composition: Transesterification product of 3-(2H-benzotriazol-2-yl)-5-(1,1-dimethylethyl)-4-hydroxy-benzenepropanoic Acid Methyl Ester with Polyglycerol A 100 ml glass flask is placed in an agitating heating block and polyglycerol (2.9 g) is transferred into the flask. 3-(2H-benzotriazol-2-yl)-5-(1,1-dimethylethyl)-4-hydroxy-benzene-propanoic acid methyl ester (8.8 g, 25 mmol) and tin-(II)-2-ethylhexanoate (0.029 g, 0.072 mmol) is added. The mixture is melted and heated up to 195° C. under a nitrogen flow. Thereafter the apparatus is slowly evacuated to a pressure of 5 mbar. The reaction mixture is stirred vigorously under vacuum at 195° C. for approx. 16 h and at 250° C. for approx. 24 h. After cooling down to ambient temperature, the UV-absorbing polymer composition (10.3 g) is obtained as a brown glassy solid.

| HPLC (unbound chromophore) | |
|---|---|
| Compound | % |
| 3-(2H-benzotriazol-2-yl)-5-(1,1-dimethylethyl)-4-hydroxy-benzene-propanoic acid methyl ester | 0 |
| 3-(2H-benzotriazol-2-yl)-5-(1,1-dimethylethyl)-4-hydroxy-benzene-propanoic acid | 1.0 |
| Sum | 1.0 |

| Solubility | | GPC | |
|---|---|---|---|
| Solvent | % | Peak RV - (ml) | 18.1 |
| C12-15 alkyl benzoate | >40 | Mn - (Daltons) | 1679 |
| Dibutyl adipate | >40 | Mw - (Daltons) | 3160 |
| Dicaprylyl carbonate | >40 | Mz - (Daltons) | 5669 |
| | | Mp - (Daltons) | 1738 |
| | | Mw/Mn | 1.88 |

Example A5

Ultraviolet Radiation Absorbing Composition: Transesterification Product of 3-(2H-benzotriazol-2-yl)-5-(1,1-dimethylethyl)-4-hydroxy-benzenepropanoic Acid Methyl Ester with Polyglycerol 3-(2H-benzotriazol-2-yl)-5-(1,1-dimethylethyl)-4-hydroxy-benzene-propanoic acid methyl ester (1000.0 g) is charged into a glass reactor equipped with nitrogen inlet, dephlegmator (120° C.) and agitation. The temperature is set to 191° C. in order to melt the 3-(2H-benzotriazol-2-yl)-5-(1,1-dimethylethyl)-4-hydroxy-benzene-propanoic acid methyl ester. As soon as the 3-(2H-benzotriazol-2-yl)-5-(1,1-dimethylethyl)-4-hydroxy-benzene-propanoic acid methyl ester is completely melted, the reactor is evacuated to 850 mbar. Molten polyglycerol (325.7 g) is charged within 1 h, while maintaining a reaction temperature of 185-190° C. Methanol is distilled of. Thereafter the vacuum is reduced gradually to 5-8 mbar at 197° C. and the reaction mass is stirred for 44 h, until the total concentration of 3-(2H-benzotriazol-2-yl)-5-(1,1-dimethylethyl)-4-hydroxy-benzene-propanoic acid methyl ester and 3-(2H-benzotriazol-2-yl)-5-(1,1-dimethylethyl)-4-hydroxy-benzene-propanoic acid is below 1.0%. The composition of the reaction mixture is monitored by HPLC. After cooling down to ambient temperature, the UV-absorbing polymer composition (1200 g) is obtained as a yellow to amber glassy solid.

| HPLC (unbound chromophore) | |
|---|---|
| Compound | % |
| 3-(2H-benzotriazol-2-yl)-5-(1,1-dimethylethyl)-4-hydroxy-benzene-propanoic acid methyl ester | 0.25 |
| 3-(2H-benzotriazol-2-yl)-5-(1,1-dimethylethyl)-4-hydroxy-benzene-propanoic acid | 0.5 |
| Sum | 0.75 | benzotriazol-2-yl)-5-(1,1-dimethylethyl)-4-hydroxy-benzene-propanoic acid methyl ester and 3-(2H-benzotriazol-2-yl)-5-(1,1-dimethylethyl)-4-hydroxy-benzene-propanoic acid is below 1.0%. The composition of the reaction mixture is monitored by HPLC. After cooling down to ambient temperature, the UV-absorbing polymer composition (384 kg) is obtained as a yellow to amber glassy solid.

| HPLC analysis of the reaction product (unbound chromophore) | |
|---|---|
| Compound | % |
| 3-(2H-benzotriazol-2-yl)-5-(1,1-dimethylethyl)-4-hydroxy-benzene-propanoic acid methyl ester | 0.1 |
| 3-(2H-benzotriazol-2-yl)-5-(1,1-dimethylethyl)-4-hydroxy-benzene-propanoic acid | 0.5 |
| Sum | 0.6 |

| HPLC analysis of the completely hydrolized reaction product | |
|---|---|
| Compound | % |
| 3-(2H-benzotriazol-2-yl)-5-(1,1-dimethylethyl)-4-hydroxy-benzene-propanoic acid | 75.8 |

| UV | | Solubility | | | GPC | |
|---|---|---|---|---|---|---|
| Wavelength (nm) | E (1%, 1 cm) | Solvent | % | | | |
| 300 | 354 | C12-15 alkyl benzoate | >40 | Peak RV-(ml) | | 18.3 |
| 320 | 292 | Dibutyl adipate | >40 | Mn-(Daltons) | | 899 |
| 340 | 351 | Dicaprylyl carbonate | >40 | Mw-(Daltons) | | 1573 |
| 360 | 269 | | | Mz-(Daltons) | | 2300 |
| 380 | 73 | | | Mp-(Daltons) | | 1354 |
| 400 | 4 | | | Mw/Mn | | 1.75 |
| 344 | 354 | | | | | |
| 344 | 354 | | | | | |
| 303 | 359 | | | | | |

Example A6

Ultraviolet Radiation Absorbing Composition: Transesterification Product of 3-(2H-benzotriazol-2-yl)-5-(1,1-dimethylethyl)-4-hydroxy-benzenepropanoic Acid Methyl Ester with Polyglycerol

3-(2H-benzotriazol-2-yl)-5-(1,1-dimethylethyl)-4-hydroxy-benzene-propanoic acid methyl ester (306.0 kg) is charged into a glass-lined steel reactor equipped with argon inlet, dephlegmator (120° C.) and agitation. The temperature is set to 195° C. in order to melt the 3-(2H-benzotriazol-2-yl)-5-(1,1-dimethylethyl)-4-hydroxy-benzene-propanoic acid methyl ester. As soon as the 3-(2H-benzotriazol-2-yl)-5-(1,1-dimethylethyl)-4-hydroxy-benzene-propanoic acid methyl ester is completely melted, the reactor is evacuated to 850 mbar and tin-(II)-2-ethylhexanoate (20.0 kg) is added. Molten polyglycerol (105.0 kg) is charged within 1-2 h, while maintaining a reaction temperature of 185-190° C. Methanol is distilled of. Thereafter the vacuum is reduced gradually to 5-8 mbar at 195° C. and the reaction mass is stirred for 72 h until the total concentration of 3-(2H-

Amount of Covalentely Bound Chromophore
75.8%−0.6%=75.2% (chromophore, determined as 3-(2H-benzotriazol-2-yl)-5-(1,1-dimethylethyl)-4-hydroxy-benzene-propanoic acid).

| UV | | Solubility in cosmetic solvents | | GPC | |
|---|---|---|---|---|---|
| E 1%, 1 cm ($\lambda$ = 344 nm) | 331 | Solvent | % | Peak RV - (ml) | 18.2 |
| Methanol (ppm) | 6 | C12-15 alkyl benzoate | >40 | | |
| $T_g$ (° C.) | 51.2 | Dibutyl adipate | >40 | Mn - (Daltons) | 756 |
| Sn (ppm) | 150 | Dicaprylyl carbonate | >40 | Mw - (Daltons) | 1464 |
| Gardner color scale | 6.2 | | | Mz - (Daltons) | 2153 |
| | | | | Mp - (Daltons) | 1320 |
| | | | | Mw/Mn | 1.94 |

The invention claimed is:
1. A method for preparing an ultraviolet radiation absorbing polymer composition comprising a polymer compound of formula (3) in an esterification/trans-esterification, which method comprises the steps of reacting a polyglycerol intermediate (2) with a benzotriazole UV-chromophore (1) comprising a complementary functional group to form the UV absorbing polyether compound (3) according to the following reaction scheme:

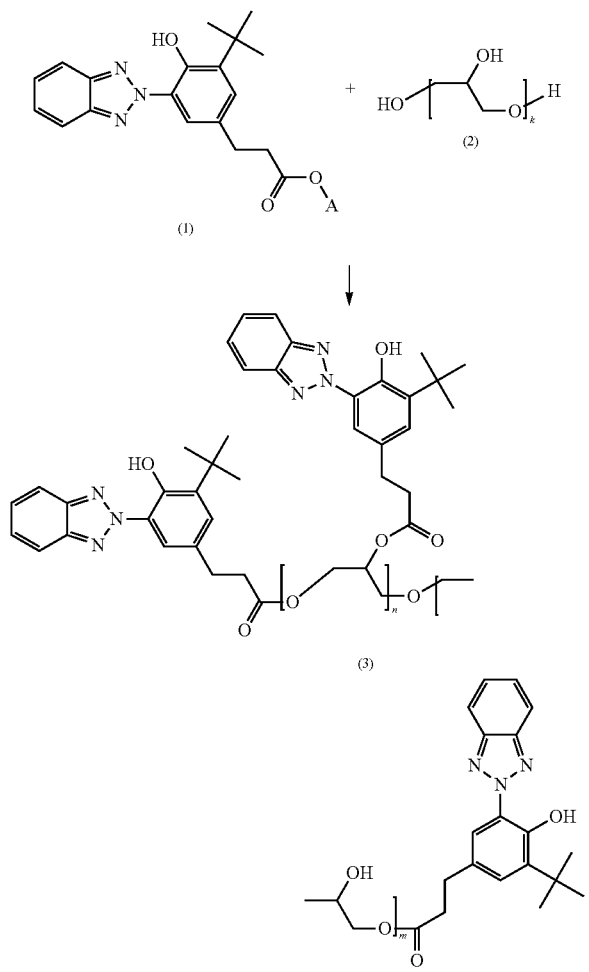

wherein
A is hydrogen; or $C_1$-$C_8$alkyl; and
k is a number from 2 to 20; and
n and m, independently from each other are a number from 0 to 20; wherein at least one of m and n is ≥1.

2. The method according to claim 1, wherein the weight average molecular weight of the polyether of formula (3) is >500.

3. The method according to claim 1, further comprising removing water or alcohol formed during the reaction by distillation during the esterification/transesterification reaction.

4. The method according to claim 1, wherein the esterification/transesterification is carried out at a temperature of 160-270° C.

5. The method according to claim 1, wherein the esterification/transesterification is carried out without any additional solvent.

6. The method according to claim 1, wherein the esterification/transesterification is carried out without additional esterification/transesterification catalysts.

7. The method according to claim 1, wherein the esterification/transesterification is carried out under intermittent or constant vacuum of less than 250 mbar.

8. The method according to claim 1, wherein the esterification/transesterification is carried out at a temperature of 190-260 ° C. for at least 16h.

9. The method according to claim 1, wherein the polyglycerol contains less than 5% of glycerol or linear and cyclic diglycerols.

10. The method according to claim 1, wherein the hydroxyl value of polyglycerol is in the range between 700 and 1100.

11. The method according to claim 1, wherein the benzotriazole UV-chromophore is benzenepropanoic acid, 3-(2H-benzotriazol-2-yl)-5-(1,1-dimethylethyl)-4-hydroxy—.

12. The method according to claim 1, wherein the benzotriazole UV-chromophore is benzenepropanoic acid, 3-(2H-benzotriazol-2-yl)-5-(1,1-dimethylethyl)-4-hydroxy—,methyl ester.

13. The method according to claim 1, wherein the final reaction product is used without further purification.

14. The method according to claim 12, wherein 1 part of polyglycerol is reacted with 2.8-3.2 parts of Benzenepropanoic acid, 3-(2H-benzotriazol-2-yl)-5-(1,1-dimethylethyl)-4-hydroxy—, methyl ester.

15. The method according to claim 11, wherein 1 part of polyglycerol is reacted with 2.8-3.2 parts of Benzenepropanoic acid, 3-(2H-benzotriazol-2-yl)-5-(1,1-dimethylethyl)-4-hydroxy—.

16. The method according to claim 1, wherein the weight average molecular weight of the polyether of formula (3) is from 1,000 to 20,000.

17. The method according to claim 1, wherein the weight average molecular weight of the polyether of formula (3) is from 1,000 to 10,000.

18. The method according to claim 1, wherein the esterification/transesterification is carried out at a temperature of 190-260° C.

19. The method according to claim 1, wherein the esterification/transesterification is carried out under intermittent or constant vacuum of less than 100 mbar.

20. The method according to claim 1, wherein the hydroxyl value of polyglycerol is in the range between 750 and 900.

* * * * *